United States Patent [19]
Mulder

[11] Patent Number: 5,550,047
[45] Date of Patent: Aug. 27, 1996

[54] OLIGONUCLEOTIDES WITH ANTI-EPSTEIN-BARR VIRUS ACTIVITY

[75] Inventor: Carel Mulder, Worcester, Mass.

[73] Assignee: University of Massachusetts, Worcester, Mass.

[21] Appl. No.: 199,510

[22] Filed: Feb. 18, 1994

[51] Int. Cl.$^6$ .............. C12N 5/00; C12N 7/06; A61K 48/00; C07H 21/04
[52] U.S. Cl. .............. 435/238; 435/240.2; 536/23.1; 536/23.72; 536/24.5; 514/44; 935/8; 935/34
[58] Field of Search .............. 514/44; 536/23.1, 536/24.5; 435/238, 240.2

[56] References Cited

U.S. PATENT DOCUMENTS

| | | | |
|---|---|---|---|
| 5,149,797 | 9/1992 | Pederson et al. | 536/27 |
| 5,149,798 | 9/1992 | Agrawal et al. | 536/27 |
| 5,194,428 | 3/1993 | Agrawal et al. | 514/44 |
| 5,242,906 | 9/1993 | Pagano et al. | 514/44 |

FOREIGN PATENT DOCUMENTS

| | | |
|---|---|---|
| WO91/12811 | 9/1991 | WIPO. |
| WO92/04903 | 4/1992 | WIPO. |
| WO93/07882 | 4/1993 | WIPO. |
| WO93/11267 | 6/1993 | WIPO. |

OTHER PUBLICATIONS

Biggin et al. (1987) *J. Virol.* 61:3120–3132
E. R. Kern (1990) In: Antiviral Agents and Viral Diseases of Man, G. J. Galusso et al, eds, pp. 94–95.
R. Baer et al (1984) *Nature* 310: 207–211.
Daibata et al. (1994) *Virology* 198:446–454.
Agrawal et al. (1992) *Gene Regulation: Biology of Antisense RNA and DNA* Erickson and Izant editors, Raven Press, Ltd., New York.
Agrawal et al. (1992) *Trends Biotechnol.* 10: 152–158.
Bergot (1992) *J. Chromatog.* 559:35–42.
Matsukura et al. in *Prospects for Antisense Nucleic Acid Therapy of Cancer and AIDS*, Wiley–Liss, Inc. (1991) pp. 159–178.
Agrawal in *Prospect for Antisense Nucleic Acid Therapy of Cancer And AIDS*, Wiley–Liss, Inc. (1991) pp. 143–158.
Mellinghoff et al. (1991) *Virology* 185:922–928.
Leiter et al. (1990) *Proc. Natl. Acad. Sci.* (USA) 87: 3430–3434.
Uhlman et al. (1990) *Chem. Rev* 90:534–583.
Takada et al. (1989) *J. Virol.* 63:445–449.
Agrawal et al. (1988) *Proc. Natl. Acad. Sci..* (USA) 85:7079–7083.
Hardwick et al. (1988) *J. Virol..* 62:2274–2284.
Agrawal et al. (1987) *Tetrahedron Lett.* 28(31):3539–3542.
Caruthers et al.(1987) *Meth. Enzymol.* 154:287–313.
Chevallier-Greco et al. (1986) *EMBO J.*5:3243–3249.
Froelhler (1986) *Tetrahedron Lett..* 27:5575–5578.
Liebermann et al. (1986) *J. Virol.* 60:140–148.
Takada et al. (1986) *J. Virol.* 57:1016–1022.
Countryman et al. (1985) *Proc. Natl. Acad. Sci.* (USA) 82:4085–4089.
Gardella et al. (1984) *J. Virol.* 50:248–254.
Takada (1984) *Int. J. Cancer* 33:27–32.
Tovey et al. (1987) *Nature* 276:270–272.
Hinuma et al. (1967) *J. Virol.* 1:1045–1051.

*Primary Examiner*—Jacqueline M. Stone
*Assistant Examiner*—Bruce R. Campell
*Attorney, Agent, or Firm*—Lappin & Kusmer

[57] ABSTRACT

Disclosed are oligonucleotides complementary to and hybridizable with a portion of the BZLF1 RNA of Epstein-Barr virus, useful for inhibiting the induction of the lytic cycle in EBV-infected cells, and in inhibiting EBV replication.

7 Claims, 6 Drawing Sheets

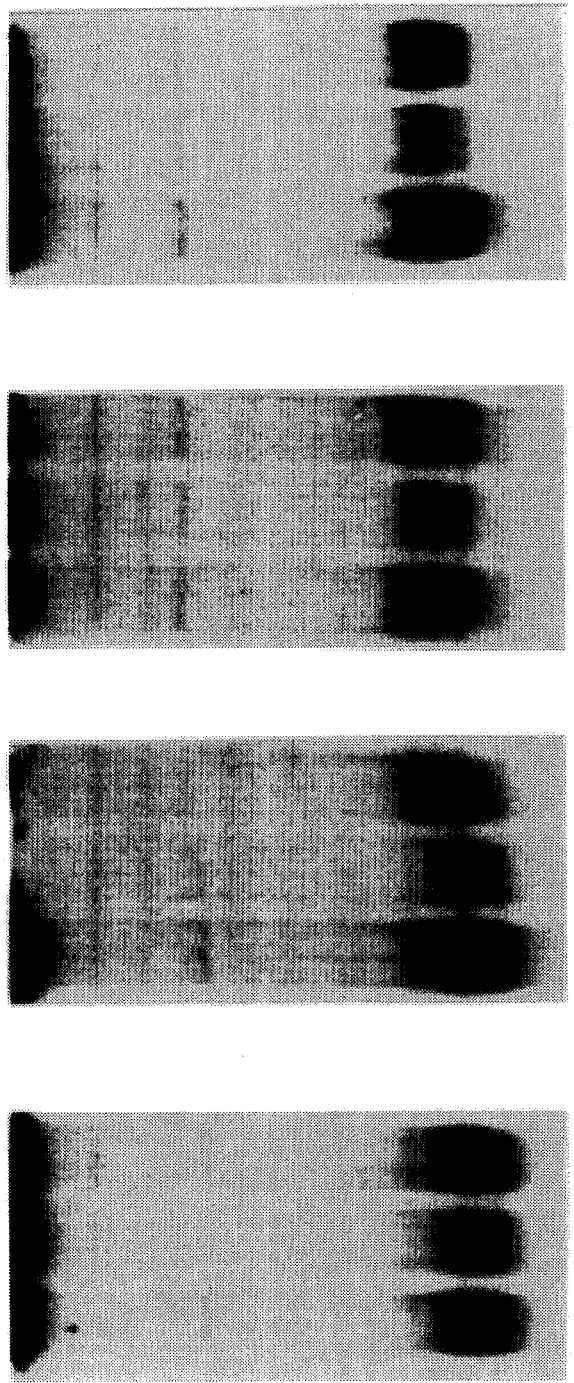

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:1:

TTTGGGTCCA TCATCTTCAG CAAAG    25

( 2 ) INFORMATION FOR SEQ ID NO:2:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:2:

CATCATCTTC AGCAAAGATA    20

( 2 ) INFORMATION FOR SEQ ID NO:3:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:3:

TCAGAAGTCG AGTTTGGGTC  20

OLIGONUCLEOTIDES WITH ANTI-EPSTEIN-BARR VIRUS ACTIVITY

BACKGROUND OF THE INVENTION

This invention relates to the treatment of Epstein-Barr virus (EBV) infection. More particularly, this invention relates to antisense oligonucleotides complementary to portions of the viral mRNA useful in inhibiting Epstein-Barr virus replication.

Epstein-Barr virus (EBV) is a human herpesvirus having a double-stranded DNA genome. It is a B lymphotrophic virus which is worldwide in distribution. Primary infection with EBV during childhood is usually subclinical. Between 25 and 70 percent of adolescents and adults who undergo a primary EBV infection develop the clinical syndrome of infectious mononucleosis. EBV is also associated with EBV syndrome, X-linked lymphoproliferative syndrome (XLP), and oral leucoplacia in AIDS patients, and with malignancies such as nasopharyngeal carcinoma, Burkitt's lymphoma, anaplastic nasopharyngeal carcinoma, Hodgkin's Disease, and hairy cell leukemia.

The diseases which have been attributed to EBV infection are diverse in part because, after entering the body via the oropharynx and entering an epithelial cell, the viral genome can replicate in alternative ways, leading to productive (lytic) or latent infection. EBV lyric infection causes the pathology related to the cytolysis of infected cells, often accompanied by the body's aberrant immunopathologic responses to viral antigens. In contrast, EBV latent infection occurs when the viral genome becomes fixed in epithelial or lymphoid cells as an episome, rather than in a viral particle. Episomes later appear in anaplastic nasopharyngeal carcinoma and in immortalized B-lymphocytes.

Productive EBV infection such as that associated with X-linked lymphoproliferative syndrome has been treated systematically with conventional anti-virus nucleoside analogs such as 9-(2-hydroxyethoxymethyl)guanine (acyclovir), 1-( 2-fluoro-2-deoxy-B-D-arabinofuranosyl)-5-iodocytosine (FIAC), several E-5-(2-bromovinyl)-2'-deoxyuridine (BVdU)-containing compounds, and (S)-9-(3-hydroxy-2-phosphonylmethoxypropyl) adenine ((S)-HPMPA) which traditionally have been used to inhibit the replication of other herpesviruses, as well as azido-thymidine (AZT) (reviewed in Pagano (in press). Pyrophosphate analogs, thymidine kinase analogs, and ribonucleoside reductase inhibitors have also been used. However, none of these drugs have been very effective in inhibiting EBV replication. In addition, the effect of these analogs is not limited to viral nucleotides, and thus unwanted side effects often present when they are used. Other therapies for EBV-associated disorders such as nasopharyngeal carcinoma have included surgery in combination with high doses of radiation. Radiation therapy has also been combined with chemotherapy in the treatment of EBV-related lymphomas, but often without much success. Thus, there remains a need for more effective treatment of EBV-related diseases which are specific for the virus, and which have few, if any, detrimental side-effects.

Recently, new chemotherapeutic agents have been developed which are capable of modulating cellular and foreign gene expression. These agents, called antisense oligonucleotides, bind to a target single-stranded nucleic acid molecules according to the Watson-Crick or the Hoogsteen rule of base pairing, and in doing so, disrupt the function of the target by one of several mechanisms: by preventing the binding of factors required for normal transcription, splicing, or translation; by triggering the enzymatic destruction of mRNA by RNase H, or by destroying the target via reactive groups attached directly to the antisense oligonucleotide.

Antisense oligodeoxynucleotides have been designed to specifically treat latent EBV infection by inhibiting the expression of the EBNA-1 gene of EBV (U.S. Patent No. 5,242,906). Antisense oligonucleotides have also been used to inhibit the expression of HIV-1, influenza, and other viruses (see, e.g., Agrawal et al., U.S. Patent No. 5,194,428; Pederson et al., U.S. Pat. Nos. 5,149,797; Agrawal (1992) Trends Biotechnol. 10:152–158; Agrawal et al. in Gene Regulation: Biology Antisense RNA and DNA (Erickson and Izant, eds.) Raven Press Ltd., New York (1992) pp. 273–283); Matsukura et al. in Prospects for Antisense Nucleic Acid Therapy of Cancer and AIDS, Wiley-Liss, Inc. (1992) pp. 159–178; and Agrawal (1991) in Prospector Antisense Nucleic Acid Therapy for Cancer and AIDS, (Wickstrom, ed.) Liss, New York, pp. 145–148).

A need for new strategies still remains for the treatment and prevention of EBV infections. In particular, compositions and therapeutic methods utilizing these compositions are desired which are effective and whose use are accompanied by little or no cellular toxicity.

SUMMARY OF THE INVENTION

Infection by EBV may result in latent or lytic infection. The activation of the lyric cycle has been found to involve several trans-activating EBV genes, BZLF1, BRLF1, and BMLF1 (Chevallier-Greco et al. (1986) EMBO J. 5:3243–3249; Hardwick et al. (1988) J. Virol. 62:2274–2284; Lieberman et al. (1986) J. Virol. 60:140–148; Takada et al. (1986) J. Virol. 57:1016–1022). However, only the BZLF1 gene, the first "immediate early" gene, by itself, is able to induce the lytic cycle in latently infected B lymphocytes, (Chevallier-Greco et al. (1986) EMBO J. 5:3243–3249; Countryman et al. (1985) Proc. Natl. Acad. Sci. (USA) 82:4085–4089; Takada et al. (1986) J. Virol. 57:1016–1022), indicating that the initial event in the lytic cycle is activation of BZLF1 transcription.

The present invention includes methods of suppressing the induction of the lytic (replicative) cycle of EBV using synthetic oligonucleotides complementary to and hybridizable with BZLF1 RNA.

As used herein, the term "synthetic oligonucleotide" includes chemically synthesized polymers of three or up to 100 and preferably from about 12 to about 60 ribonucleotide and/or deoxyribonucleotide monomers connected together or linked by at least one 5' to 3' internucleotide linkage.

In some aspects of the invention, the oligonucleotides are modified. The term "modified oligonucleotide" is used herein as an oligonucleotide in which at least two of its nucleotides are covalently linked via a synthetic linkage, i.e., a linkage other than a phosphodiester between the 5' end of one nucleotide and the 3' end of another nucleotide in which the 5' nucleotide phosphate has been replaced with any number of chemical groups. Preferable synthetic linkages include alkylphosphonates, phosphorothioates, phosphorodithioates, alkylphosphonothioates, phosphoramidates, phosphate esters, carbamates, carbonates, phosphate triesters, acetamidate, and carboxymethyl esters. In one preferred embodiment of the invention, the oligonucleotide comprises at least one phosphorothioate linkage.

The term "modified oligonucleotide" also encompasses oligonucleotides with a modified base and/or sugar. For example, a 3', 5'-substituted oligonucleotide is a modified oligonucleotide having a sugar which, at both its 3' and 5' positions is attached to a chemical group other than a hydroxyl group (at its 3' position) and other than a phosphate group (at its 5' position). A modified oligonucleotide may also be a capped species. In addition, unoxidized or partially oxidized oligonucleotides having a substitution in one non-bridging oxygen per nucleotide in the molecule are also considered to be modified oligonucleotides. Also considered as modified oligonucleotides are oligonucleotides having nuclease resistance-conferring bulky substituents at their 3' and/or 5' end(s) and/or various other structural modifications not found in vivo without human intervention are also considered herein as modified.

The oligonucleotides of the invention are complementary to a portion of the EBV RNA transcribed from the immediate early BZLF1 gene. The oligonucleotides hybridize to the RNA under normal physiological conditions existing within a cell harboring the RNA. Such conditions include pH, temperature, and ionic conditions.

The portion of the BZLF1 RNA to which the oligonucleotides of the invention are complementary includes any region of the RNA. This region is at least 6, and preferably 12 to 60 nucleotides in length. In most preferred aspects of the invention, the oligonucleotides are 15 to 25 nucleotides in length. In some particular embodiments, the region includes (starting from the 5' end of the mRNA) nucleotides $1 \geq 25$ (flanking the initiation codon (AUG), and having the nucleotide sequence set forth in the Sequence Listing as SEQ ID NO:1. In other embodiments, the oligonucleotide of the invention has a sequence which is complementary to the region starting with the 5' untranslated region and ending with the two copies of AUG with which the open reading frame begins, and having nucleotide SEQ ID NO:2. In yet another embodiment, the oligonucleotide has a sequence complementary to a region immediately downstream of the translational initiation codon of the mRNA derived from the BZLF1 gene, and has SEQ ID NO:3.

In some aspects, the invention provides an oligonucleotide which has antiviral activity against EBV lyric replication effected by hybridization with a portion of the mRNA. In others, a pharmaceutical composition including at least one of the oligonucleotides of the invention, and a pharmaceutically acceptable carrier are provided.

The pharmaceutical composition is used in a method of inhibiting, preventing, and/or reducing EBV replication in a cell. In this method, a therapeutic amount of the pharmaceutical composition is administered to the cell which is to be protected from lyric infection or treated for an existing infection. The oligonucleotide in the pharmaceutical composition enters the cell, wherein it hybridizes to EBV DNA or RNA, thereby inhibiting EBV replication and thus lytic infection. The pharmaceutical composition is also utilized in a method of treating EBV infection wherein the composition is administered to an infected mammal or cell.

BRIEF DESCRIPTION OF THE DRAWINGS

The foregoing and other objects of the present invention, the various features thereof, as well as the invention itself may be more fully understood from the following description, when read together with the accompanying drawings in which:

FIG. 5A is an autoradiogram showing effect of 100 μg/ml modified antisense or control oligonucleotides on EBV DNA synthesis of P3HR-1 cells at day 0 which were then subcultured every 2 days in medium containing 100 μg/ml oligonucleotide: lanes 1, no oligonucleotide treatment; lanes 2, modified antisense oligonucleotide; lanes 3, modified control oligonucleotide. The numbers under each lane are the fractional amounts of counts in the linear (L) EBV DNA range compared with the counts in lanes 1.

DETAILED DESCRIPTION OF THE PREFERRED EMBODIMENTS

Figure 1:
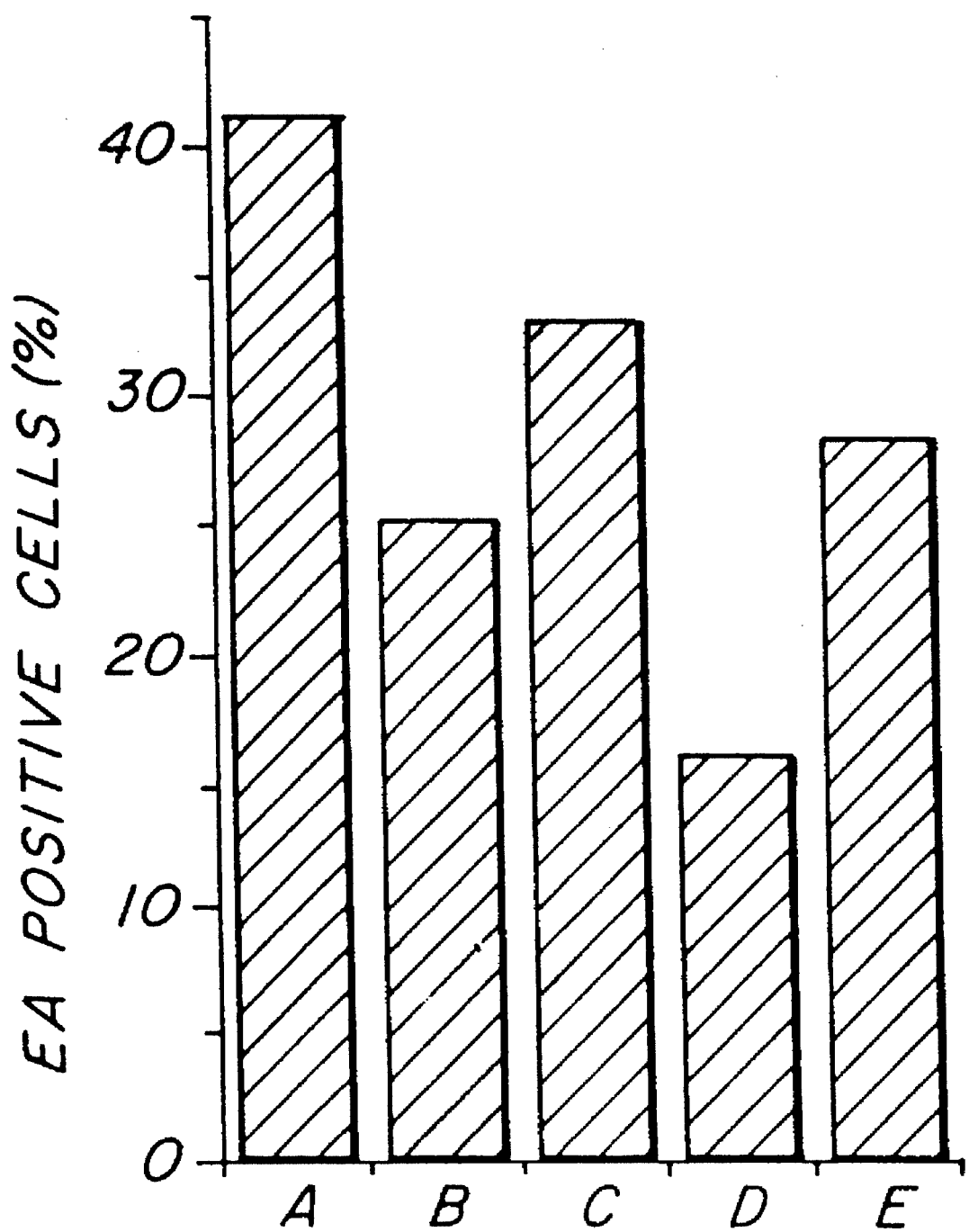
FIG. 1 is a graphic representation of the effect that no oligonucleotide treatment (A), a modified antisense oligonucleotide of the invention (B), a modified control oligonucleotide (C), a phosphodiester (PO)-linked (unmodified) oligonucleotide of the invention (D), and an unmodified control oligonucleotide (E) has on the expression of the $EA_D$ gene in EBV-infected cells.

The patent and scientific literature referred to herein establishes the knowledge that is available to those with skill in the art. The issued U.S. patent and allowed applications cited herein are hereby incorporated by reference.

EBV has a double stranded DNA genome. During latency, this genome is circular; in the virion, and therefore during productive (lytic) infection, it is linear. BZLF1 is the first immediate early (IE) gene of EBV. Its translation product, ZEBRA, transactivates other IE genes whose products transactivate early (EA) genes. Most EA gene products are required for viral DNA synthesis. Once viral DNA synthesis starts, a third set of lytic viral genes are activated, the late (LA) genes, whose products are mainly viral particle (virion) proteins such as viral capsid antigen (VCA), the major capsid protein.

Activation of this entire lytic cycle can be prevented by the suppression of BZLF1 expression. Accordingly, the present invention relates to methods of suppressing BZLF1 expression by means of oligonucleotides which are sufficiently complementary to regions of the EBV BZLF1 RNA such that, under normal physiological conditions existing in the cell, they hybridize to those regions. Hybridization renders the mRNA unavailable to serve as a template for translation of protein, and as a result, EBV lytic infection and replication is inhibited.

The oligonucleotides may be targeted to any region of the BZLF1 transcript. An example of such oligonucleotide includes one complementary to the region including (starting from the 5' end of the mRNA) nucleotides 1–25 flanking the initiation codon AUG and having the nucleotide sequence set forth in the Sequence Listing as SEQ ID NO:1. Another example is an oligonucleotide having a sequence complementary to the region starting with the 5' untranslated region and ending with the two copies of AUG with which the open reading frame begins. Such as oligonucleotide can have the nucleotide sequence set forth in the Sequence listing as SEQ ID NO:2. Yet another example is an the oligonucleotide having a sequence complementary to a region immediately downstream of the translational initiation codon of the mRNA derived from the BZLF1 gene. An oligonucleotide sequence fitting this description is set forth in SEQ ID NO:3.

Oligonucleotides of the invention are composed of deoxyribonucleotides, ribonucleotides, or a combination of both, with the 5' end of one nucleotide and the 3' end of another nucleotide being covalently linked. These oligonucleotides are at least 6 nucleotides in length, but are preferably 10 to 50 nucleotides long, with 15 to 25 mers being the most common. These oligonucleotides can be prepared by the art recognized methods such as phosphoramidate or H-phosphonate chemistry which can be carried out manually or by an automated synthesizer as described in Uhlmann et al. (Chem. Rev. (1990) 90:534–583).

The oligonucleotides of the invention may also be modified in a number of ways without compromising their ability to hybridize to BZLF1 mRNA. For example, the oligonucleotides may contain other than phosphodiester internucleotide linkages between the 5' end of one nucleotide and the 3' end of another nucleotide in which the 5' nucleotide phosphate has been replaced with any number of chemical groups. Examples of such chemical groups include alkylphosphonates, phosphorothioates, phosphorodithioates, alkylphosphonothioates, phosphoramidates, phosphate esters, carbamates, acetamidate, carboxymethyl esters, carbonates, and phosphate triesters. Oligonucleotides with these linkages can be prepared according to known methods (see, e.g., Uhlmann et al. (1990) Chem. Rev. 90:543–583).

Other modifications include those which are internal or at the end(s) of the oligonucleotide molecule and include additions to the molecule of the internucleoside phosphate linkages, such as cholesteryl or diamine compounds with varying numbers of carbon residues between the amino groups and terminal ribose, deoxyribose and phosphate modifications which cleave, or crosslink to the opposite chains or to associated enzymes or other proteins which bind to the viral genome. Examples of such modified oligonucleotides include oligonucleotides with a modified base and/or sugar such as arabinose instead of ribose, or a 3', 5-substituted oligonucleotide having a sugar which, at both its 3' and 5' positions is attached to a chemical group other than a hydroxyl group (at its 3' position) and other than a phosphate group (at its 5' position). Other modified oligonucleotides are capped with a nuclease resistance-conferring bulky substituent at their 3' and/or 5' end(s), or have a substitution in one nonbridging oxygen per nucleotide. Such modifications can be at some or all of the internucleoside linkages, as well as at either or both ends of the oligonucleotide and/or in the interior of the molecule.

The preparation of these unmodified and modified oligonucleotides is well known in the art (reviewed in Agrawal et al. (1992) Trends Biotechnol. 10:152–158). For example, nucleotides can be covalently linked using art-recognized techniques such as phosphoramidate, H-phosphonate chemistry, or methylphosphoramidate chemistry (see, e.g., Uhlmann et al. (1990) Chem. Rev. 90:543–584; Agrawal et al. (1987) Tetrahedron. Lett. 28:(31):3539–3542); Caruthers et al. (1987) Meth. Enzymol. 154:287–313; U.S. Pat. No. 5,149,798). Oligomeric phosphorothioate analogs can be prepared using methods well known in the field such as methoxyphosphoramidite (see, e.g., Agrawal et al. (1988) Proc. Natl. Acad. Sci. (USA) 85:7079–7083) or H-phosphonate (see, e.g., Froehler (1986) Tetrahedron Lett. 27:5575–5578) chemistry. The synthetic methods described in Bergot et al. (J. Chromatog. (1992) 559:35–42) can also be used.

A demonstration of the antiviral effect of individual oligonucleotides and methods of the invention is described below.

When EBV infects B lymphocytes, the cells become immortalized due to the activation of the latent cycle. Some of the immortalized B cells can become malignant, which is thought to lead to such malignancies as Burkitt's Lymphoma. One such immortalized cell line is the Akata cell line which is a Type I Burkitt's Lymphoma cell line. It has been discovered that anti-IgG crosslinking of such lymphoma, as well as other specific interventions, triggers the transition of the latent phase to the lytic cycle by inducing/activating BZLF1. Thus, these cells are useful for testing the ability of various oligonucleotides to inhibit the onset of the lytic cycle and EBV productive replication.

In order to determine if antisense oligonucleotides to BZLF1 inhibit productive EBV replication, such a lymphoma cell line was treated with four different concentrations (4, 20, 100 and 200 μg/ml) of unmodified or modified oligonucleotide complementary to BZLF1 mRNA, or with a modified or unmodified control oligonucleotide and then with anti-IgG immunoglobulin to induce the lyric cycle (Takada (1984) Int. J. Cancer 33:27–32; Tovey et al. (1978) Nature 276:270–272). Inhibition of EBV replication was determined by measuring the activation of the $EA_D$ gene by counting the percentage of $EA_D$-positive cells under fluorescent light after staining the cells with human serum, counter-stained with fluorescein labelled goat-antihuman serum.

Representative results for $EA_D$ induction after treatment with 100 μg/ml oligonucleotide are shown in the bar graph in FIG. 1. The results for $EA_D$ induction after treatment with different concentrations of oligonucleotide are shown as the dose-response curves in FIGS. 2A and 2B. These results demonstrate that both modified and unmodified oligonucleotides complementary to portions of the BZLF1 RNA (the "antisense" oligonucleotide) inhibit $EA_D$ induction more efficiently that do the modified and unmodified control oligonucleotides. Furthermore, modified antisense oligonucleotides at 20 μg/ml has about the same effect as unmodified antisense oligonucleotides at 200 μg/ml, probably due to the short halflife of the unmodified oligonucleotides (having phosphodiester internucleotide linkages) in the cell.

Another way to measure the ability of oligonucleotides of the invention to inhibit EBV replication is to measure EBV DNA synthesis and to determine the conformation that the newly synthesized DNA assumes. During latency, the DNA is circular; during lyric infection, the DNA assumes a linear conformation. Measurement of DNA synthesis and conformation can be accomplished as follows. Briefly, $10^6$ μg/ml cells treated with no oligonucleotides (untreated) or with four different concentrations of either an unmodified or modified control or antisense oligonucleotide (as described above), or 5 ml of the cell supernatants from each untreated or treated cell batch, were loaded into the wells of a Gardella gel (J. Virol. (1984) 50:248–254) as described in the examples below. The supernatants are monitored to detect virus release from the cells. The gels after transfer and hybridization with a $^{32}$P-labelled EBV probe were counted for $^{32}$p in the linear and circular EBV DNA range, and subjected to autoradiography. The cpm of the $^{32}$p are shown in TABLE 1. This Table also lists the ratio of counts in the linear EBV DNA range in the gels, compared to their respective untreated (control) cells and also after partially correcting the control results for the variations seen.

oligonucleotides reduces the percentage VCA-positive cells to 22% and 16% at 100 μg/ml and 200 μg/ml, respectively, while treatment with control oligonucleotides has less of an inhibitory effect than either modified or unmodified antisense oligonucleotide.

It is known that BZLF1 mRNA can be found in the nucleus of Akata cells 20 minutes after induction by IgG (Mellinghoff et al. (1991) Virol. 185:922–928). Thus, to determine to determine the most effective time to treat the cells with the antisense oligonucleotide of the invention, untreated Akata cells or Akata cells treated with various control or antisense oligonucleotides at different times before induction with IgG were subjected to gel analysis to determine the extent of DNA synthesis as described above.

Figure 4:
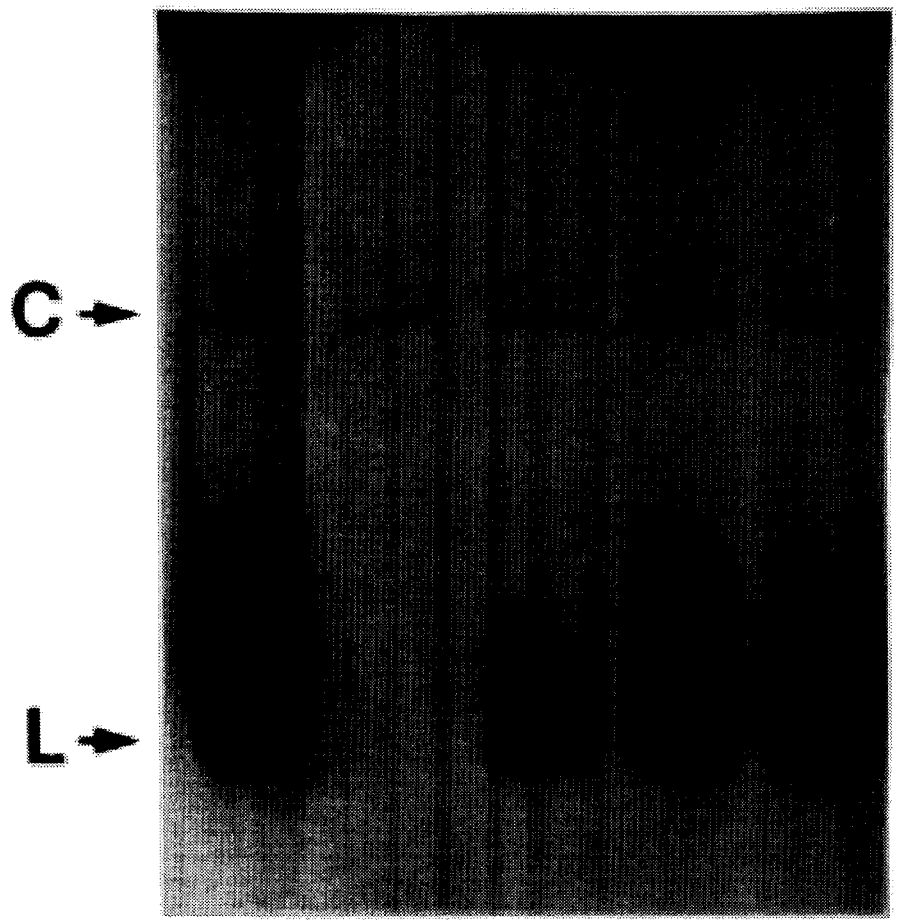
FIG. 4 is a autoradiogram showing the effect on EBV DNA synthesis of adding 100 μg/ml modified antisense oligonucleotides to Akata cells at different times after activation of the lyric cycle by IgG: lane 1, induced cells, no oligonucleotides; lane 2, uninduced cells; lane 3, antisense oligonucleotides added 3 hours before IgG activation of the lytic cycle; lane 4, antisense oligonucleotides added at the same time as IgG activation; lane 5, antisense added 3 hours after IgG activation. The numbers under each lane are the fractional amounts of counts in the linear (L) EBV DNA range compared with the counts in lane 1.

The results are shown in FIG. 4. The numbers under each lane are the fractional amounts of counts in the linear (L) EBV DNA range compared to the counts detected in untreated, induced cells (lane 1). These results show that the addition of antisense oligonucleotide to BZLF1 mRNA 3 hours before IgG activation of the lytic cycle reduces viral DNA synthesis over two fold in comparison with the addition of oligonucleotide added at the same time or three hours after IgG activation. Thus, the most effective time to treat latently effected cells is before induction.

Like the Akata cells mentioned above, P3HR-1 cells are also useful for testing the ability of various oligonucleotides

TABLE I

|  | 4 μg/ml | | 20 μg/ml | | 100 μg/ml | | 200 μg/ml | |
| --- | --- | --- | --- | --- | --- | --- | --- | --- |
|  | CPM | Ratio | CPM | Ratio | CPM | Ratio | CPM | Ratio |
| No antisense | 39 | 1.00 | 75 | 1.00 | 146 | 1.00 | 88 | 1.00 |
| modified antisense | 34 | 0.86 | 20 | 0.27 | 33 | 0.23 | 24 | 0.26 |
| modified control | 43 | 1.09 | 57 | 0.76 | 149 | 1.01 | 60 | 0.69 |
| unmodified antisense | 47 | 1.20 | 82 | 1.09 | 116 | 0.79 | 32 | 0.37 |
| unmodified control | 64 | 1.60 | 78 | 1.04 | 164 | 1.12 | 117 | 1.3 |

These results show that EBV DNA replication is reduced by 73% when infected cells are treated with 20 μg/ml modified antisense oligonucleotides, with little variation at higher concentrations, and is reduced by 63% when 200 μg/ml unmodified antisense oligonucleotide was used. In contrast, modified and unmodified unrelated (control) oligonucleotides have little or no inhibitory effect on replication.

Yet another way to measure the ability of the antisense oligonucleotides of the invention to inhibit EBV replication is to measure the presence of the late gene product viral capsid antigen (VCA), the major capsid protein. Using the same Akata cells treated as described above, slides were made, frozen, and stained for VCA using fluorescently labelled antibody to VCA. The percentage of VCA-positive cells are then counted and plotted versus the oligonucleotide concentration used.

Figure 2A:
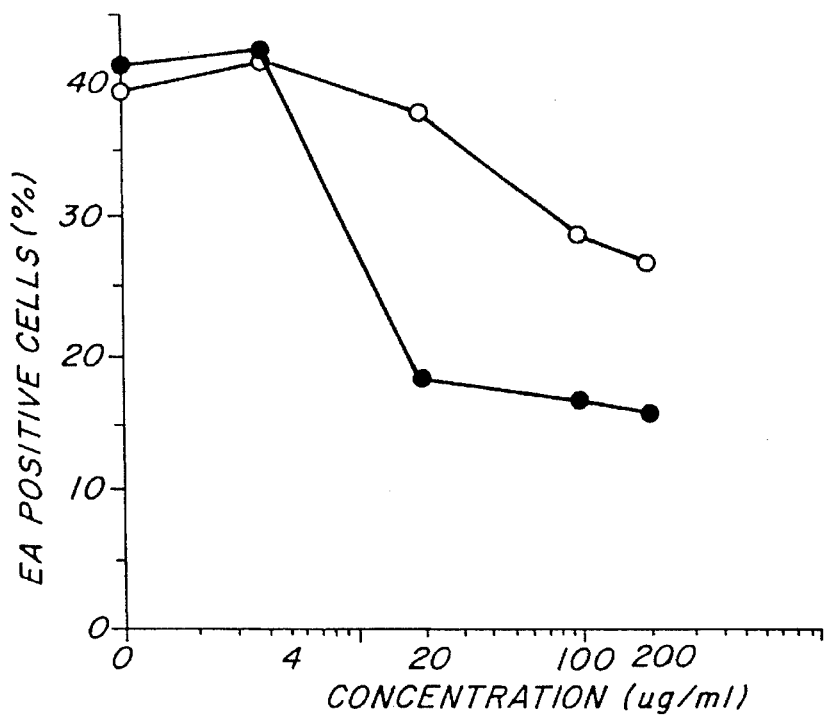
FIG. 2A is a graphic representation of the induction of $EA_D$ in EBV-infected cells treated with different concentrations of unmodified control (—o—) or unmodified antisense (—●—) oligonucleotides.
Figure 2B:
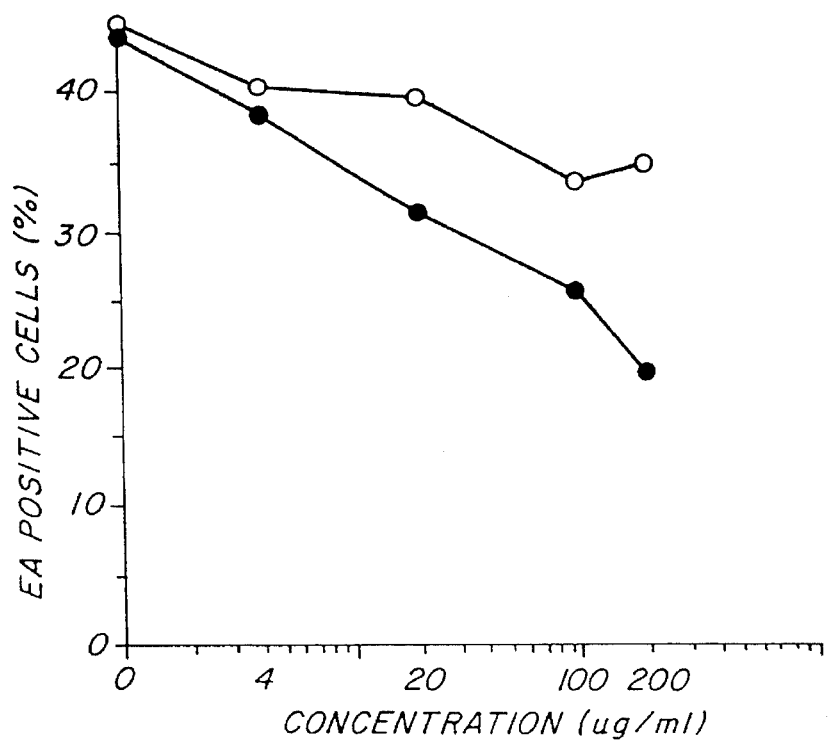
FIG. 2B is a graphic representation of the induction of $EA_D$ in EBV-infected cells treated with different concentrations of modified control (—o—) or modified antisense (—●—) oligonucleotides.
Figure 3A:
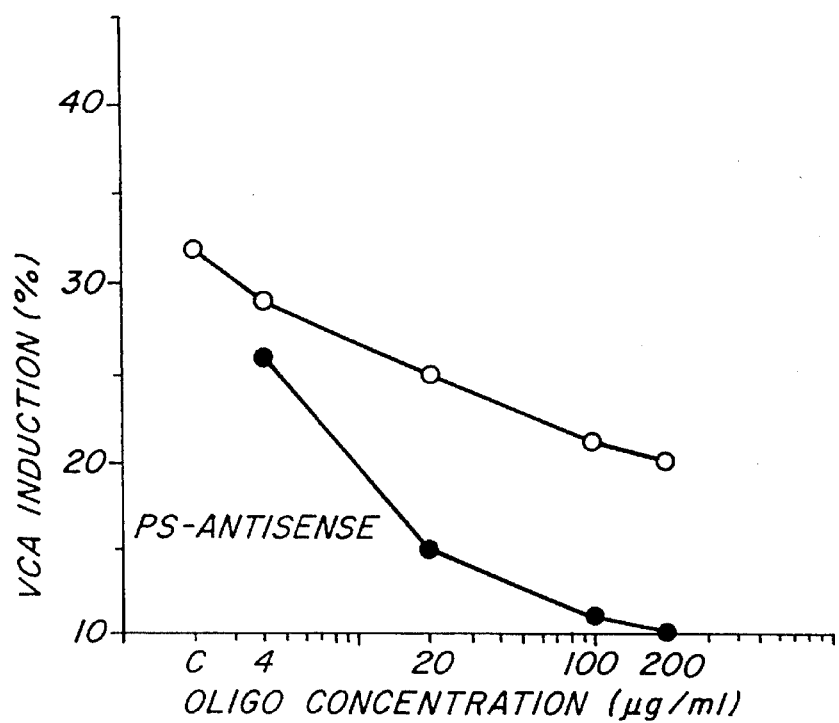
FIG. 3A is a graphic representation of the induction of VCA in EBV-infected cells treated with different concentrations of modified control (—o—) or modified antisense (—●—) oligonucleotides.
Figure 3B:
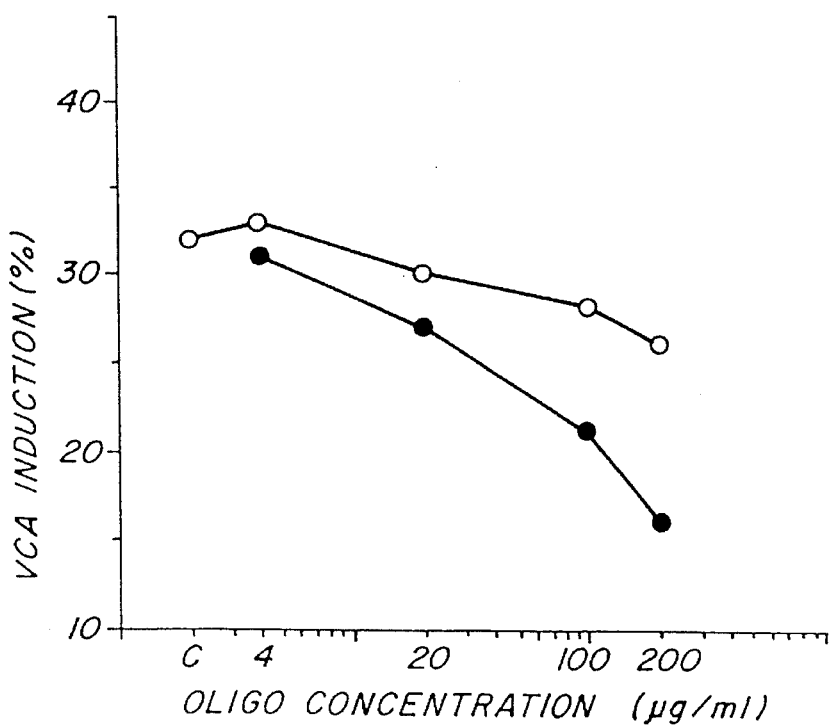
FIG. 3B is a graphic representation of the induction of VCA in EBV-infected cells treated with different concentration of unmodified control (—o—) or unmodified antisense (—●—) oligonucleotides.

The results shown graphically in the dose response curves in FIGS. 3A and 3B are quantitatively similar to the $EA_D$ staining shown in FIGS. 2A and 2B: 32% of the induced cells are VCA-positive when untreated; when treated with modified antisense oligonucleotide, the percentage of VCA-positive cells is reduced in a dose-dependent fashion to 15%, 12%, and 10% at 20 μg/ml, 100 μg/ml, and 200 μg/ml, respectively. Similarly, treatment with unmodified antisense to inhibit lyric replication. P3HR-1 is another cell line derived from Burkitt's Lymphoma. This line produces EBV even when uninduced. Furthermore, because the virus in these cells is temperature sensitive, infected cells produce more virus at 33° C. than at 37° C.

Figure 5B:
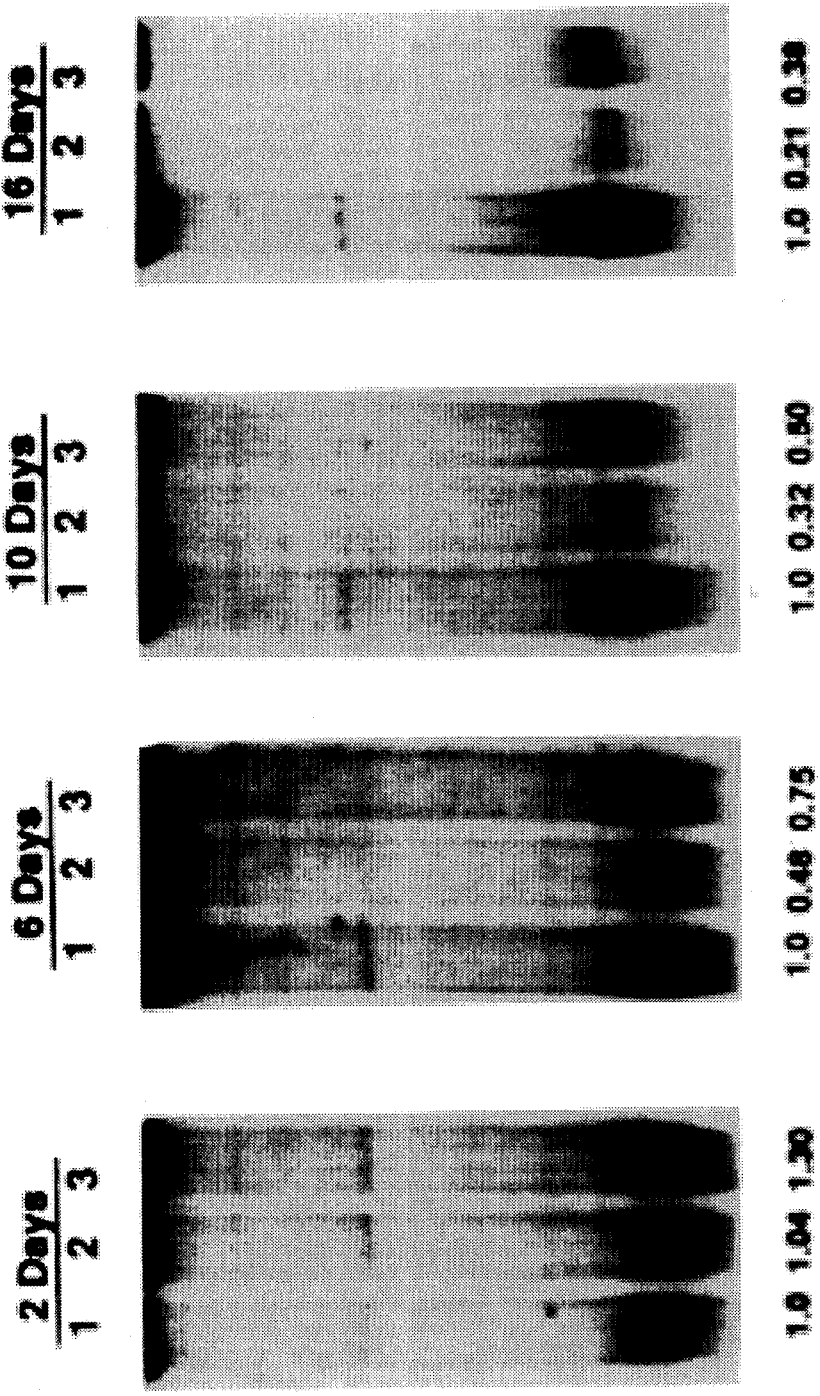
FIG. 5B is an autoradiogram showing effect of 200 μg/ml modified antisense or control oligonucleotides on EBV DNA synthesis in P3HR-1 cells at day 0 which were then subcultured every 2 days in medium containing 200 μg/ml oligonucleotide: lanes 1, no oligonucleotide treatment; lanes 2, modified antisense oligonucleotide; lanes 3, modified control oligonucleotide. The numbers under each lane are the fractional amounts of counts in the linear (L) EBV DNA range compared with the counts in lanes 1.

When uninduced P3HR-1 cells are treated with modified antisense oligonucleotides at 100 μg/ml or 200 μg/ml at day 0, subcultured every 2 days with medium containing 100 μg/ml or 200 μg/ml oligonucleotide, respectively at 33° C., and the amounts of linear (L) and circular (C) EBV DNA measured by detecting the counts of $^{32}$p in Gardella gels as described above, EBV DNA synthesis is shown to be inhibited. The results are shown in the autoradiograms in FIGS. 5A and 5B. The numbers under each lane are the fractional amount of counts in the linear (L) EBV DNA range compared to the counts in cells not treated with antisense oligonucleotide. FIG. 5B demonstrates that 200 μg/ml modified antisense oligonucleotide reduces the amounts of EBV DNA synthesis 52%, 68%, and 79% at days 6, 10 and 16, respectively, in contrast to the control modified oligonucleotides which reduce DNA synthesis to a lesser extent.

Thus, the modified and unmodified oligonucleotides of the invention have been demonstrated to have the ability to inhibit the onset of EBV lytic replication in latently infected cells, and to inhibit further EBV replication in cells already producing virus. Therefore, these oligonucleotides are useful for preventing lytic replication by EBV in latently infected cell cultures, thereby keeping the cell culture in a latently infected state.

That the oligonucleotides of the invention are not toxic to the cells was determined by comparing the rate of $^3$H-thymidine incorporation into the newly synthesized DNA of oligonucleotide-treated cells and untreated cells. There is no difference in the rate of DNA synthesis, indicating the relative health of the cells.

The present invention further provides a therapeutic composition having antiviral activity against EBV lytic infection. The composition includes at least an oligonucleotide of the present invention, along with a physiologically acceptable carrier.

As used herein, a "physiologically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

This therapeutic formulation may be used to inhibit, reduce or prevent the replication of EBV in cells through the activity of the oligonucleotides in the composition. EBV-infected cells are then treated with the therapeutic formulation in an amount sufficient to enable the binding of the oligonucleotide to the RNA in the infected cells. In this way, the binding of the oligonucleotide to the EBV RNA inhibits the expression and replication of the virus.

The oligonucleotides of the invention may also be used to treat EBV infection in humans. In this method, the composition is administered once in a therapeutically effective amount or repeatedly in less than therapeutic amounts. Administration may be by intravenous or intraperitoneal injection, or by intranasal, oral, transdermal, or subcutaneous administration. Effective dosages of the oligonucleotide and modes of its administration in the treatment of EBV can be determined by routine experimentation. The pharmaceutical forms suitable for injectable or other use include sterile aqueous solutions or dispersions and sterile powders for the extemporaneous preparation of sterile injectable solutions or dispersions. In all cases the form must be sterile. It must be stable under the conditions of manufacture and storage and may be preserved against the contaminating action of microorganisms, such as bacterial and fungi. The carrier can be a solvent or dispersion medium. The prevention of the action of microorganisms can be brought about by various antibacterial and antifungal agents. Prolonged absorption of the injectable therapeutic agents can be brought about by the use of the compositions of agents delaying absorption.

The following examples illustrate the preferred modes of making and practicing the present invention, but are not meant to limit the scope of the invention since alternative methods may be utilized to obtain similar results.

EXAMPLES

1. Cell Lines

Akata (Takada et al. (1989) J. Virol. 63:445–449), an EBV-nonproducer Burkitt's lymphoma cell line, and P3HR-1 (Hinuma et al. (1967) J. Virol. 1:1045–1051), an EBV-producer cell line, were maintained in RPMI 1640 medium supplemented with penicilline (100 IU/ml), streptomycin (100 µg/ml), and 10% heat-inactivated fetal calf serum in a humidified atmosphere of 5% $CO_2$ in air. Akata and P3HR-1 cells were passaged at 37° C. and 33° C., respectively. The production of P3HR-1 cells is higher upon incubation at 33° C. than at 37° C.

2. Oligonucleotides

Unmodified (phosphodiester-linked (PO)) and modified (phosphorothioate-linked) (PS) oligonucleotides were synthesized by H-phosphonate chemistry using on an automated DNA synthesizer. These oligonucleotides were purified as described in U.S. patent application Ser. No. 07/311,111 ("METHOD OF SEPARATING OLIGONUCLEOTIDES FROM A MIXTURE," by GAgrawal and Zamecnik, filed Feb. 15, 1989, U.S. Pat. No. 5,352,578. A 25-mer oligonucleotide having the sequence 5'-TTT GGG TCC ATC ATC TTC AGCAAAG-3' (SEQ ID NO:1), which is the flanking sequence of the translational initiation codon (AUG) of BZLF1 transcript, was used as a BZLF1 antisense oligonucleotide. Two other BZLF1 antisense oligonucleotides which are immediately adjacent to each other and partially overlap with the SEQ ID NO:i antisense oligonucleotide were also tested: the 20mer 5'-CAT CAT CTT CAG CAA AGA TA-3' (SEQ ID NO:2) and the 20mer 5'-TCA GAA GTC GAG TTT GGG TC-3' (SEQ ID NO:3). SEQ ID NO:2 antisense oligonucleotide is complementary to the sequence starting with the 5' untranslated region and ending with the two copies of AUG with which the open reading flame starts. SEQ ID NO:3 antisense oligonucleotide hybridizes to a region immediately downstream of the translational initiation codon of the mRNA derived from the BZLF1 gene. 25mer modified (phosphorothioate-linked) and PO-linked oligonucleotides with unrelated random sequences were employed as controls.

3. Oligonucleotide Treatment of Cells

Logarithmically growing Akata cells were resuspended to a final concentration of $1\times10^6$ cells/ml with fresh medium. The cells were incubated in the presence of various concentration of modified or PO-linked antisense of control oligonucleotides for 3 hours at 37° C. in 5% $CO_2$, and then stimulated with anti-human IgG antibodies (Cappel, West Chester, Pa.) at a concentration of 100 µg/ml for 24 hours.

For the treatment of P3HR-1 cells with modified oligonucleotides, the cells ($1\times10^6$ cells/ml) received the oligonucleotides at the indicated concentrations, and the incubations were continued for 2 days at 33° C. in 5% $CO_2$. Every other day cell number was counted, and aliquots were taken for assay by EBV DNA analysis and immunofluorescence. After adjustment of the cell concentration to $1\times10^6$ cells/ml by adding fresh medium, the cells were treated again with modified oligonucleotides. Up to 9 treatments over a period of 18 days were performed.

4. EBV DNA Analysis

The form and quantity of EBV DNA were determined by gel electrophoresis and genomic hybridization of the blotted electrophoretic patterns (Gardella et al. (1984) J. Virol. 50:248–254). Briefly, $0.5\times10^6$ and $1.0\times10^6$ cells were suspended in 100 µl of sample buffer containing 15% Ficoll and 0.01% bromophenol blue in TBE buffer (89 mM Tris, 89 mM boric acid, 2.5 mM EDTA, pH 8.3) and loaded into the well of a vertical 0.75% agarose gel. Lysis buffer (100 µl), containing 5% Ficoll, 1% sodium dodecyl sulfate (SDS), 1.5 mg of pronase per ml, and 0.05% xylene cyanol green in TBE buffer, was layered over the samples. Electrophoresis was carried out at 20 V for 2 hours and then at 80 V for 16 hours at 4° C. The DNA in the gel was partially depurinated with 0.35M HCl, denatured with 0.4M NaOH in 0.5M NaCl, and transferred to nylonmembrane filters using an alkaline transfer protocol. The papers were baked at 80° C. for 1 hour, treated with prehybridization buffer, and hybridized with a random-primed $^{32}$P-labeled EBV BamHI-W probe. After being washed to remove unhybridized probe, the filters were exposed to Kodak XAR films at −80° C. with intensifying screens.

5. Immunofluorescence

Indirect immunofluorescence was used for staining of early antigen (EA) and viral capsid antigen (VCA). EA or VCA was detected, respectively, with a serum (anti-EA 1:320; anti-VCA 1:320) from a patient with nasopharyngeal carcinoma, or with a seropositive serum (anti-VCA 1:160; antiEA less than 1:10) from a healthy donor. Cells were washed with phosphate buffered saline (PBS) and spotted on a glass slide, dried, and fixed in chilly acetone for 15 minutes. The fixed smears were incubated with the serum at 37° C. for 40 minutes. After being washed in PBS, the slides were incubated with the FITC-conjugated goat anti-human IgG (Cappel, West Chester, Pa.) at 37° C. for 40 minutes. The slides were washed and mounted in 1:1 glycerol/PBS, and examined under a fluorescence microscope. At least 500 cells were counted for each determination.

6. Incorporation of $^3$H-Thymidine

Either stimulated or unstimulated Akata cells ($2\times10^6$) were incubated with modified or PO-linked oligonucleotides for 24 hours. The cells were then pulsed with 1 µCi of $^3$H-thymidine (NEN/DuPont) for 4 hours at 37° C. After brief cell lysis with 0.4M NaOH, the lysates were placed on fiberglass filtermats and washed extensively. The dried filters were transferred to scintillation vials containing 3 ml of scintillant and counted.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A synthetic oligonucleotide complementary to and hybridizable with a portion of the BZLF1 RNA of Epstein-Barr virus, the oligonucleotide having the nucleotide sequence set forth as SEQ ID NO:1 or SEQ ID NO:3.

2. The oligonucleotide of claim 1 which is a modified oligonucleotide selected from the group consisting of an oligonucleotide with at least one synthetic internucleotide linkage, a 3',5'-substituted oligonucleotide, a capped oligonucleotide, an unoxidized oligonucleotide, a partially oxidized oligonucleotide, a nuclease-resistant oligonucleotide, a cholesteryl-containing oligonucleotide, a diamine-containing oligonucleotide, and an arabinose-substituted oligonucleotide.

3. The oligonucleotide of claim 1 comprising at least one internucleotide linkage selected from the group consisting of alkylphosphonate, phosphorothioate, phosphorodithioate, alkylphosphonothioate, phosphoramidate, phosphate ester, carbamate, carbonate, phosphate triester, acetamidate, and carboxymethyl ester.

4. The oligonucleotide of claim 3 comprising at least one phosphorothioate internucleotide linkage.

5. The oligonucleotide of claim 1 which comprises at least one deoxyribonucleotide.

6. The oligonucleotide of claim 1 which comprises at least one ribonucleotide.

7. A method of inhibiting Epstein-Barr virus replication in a cell in vitro comprising the step of treating the cell with the oligonucleotide of claim 1.

* * * * *